US008940521B2

(12) United States Patent
Murray et al.

(10) Patent No.: US 8,940,521 B2
(45) Date of Patent: Jan. 27, 2015

(54) COMPOSITE DETECTION DEVICES HAVING IN-LINE DESALTING AND METHODS OF MAKING THE SAME

(75) Inventors: Anthony John Murray, Lebanon, NJ (US); Anping Zhang, Rexford, NY (US); Rui Chen, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 1626 days.

(21) Appl. No.: 11/947,224

(22) Filed: Nov. 29, 2007

(65) Prior Publication Data
US 2009/0142825 A1 Jun. 4, 2009

(51) Int. Cl.
| | |
|---|---|
| B01D 63/08 | (2006.01) |
| B01D 69/10 | (2006.01) |
| B01D 71/02 | (2006.01) |
| B01D 71/04 | (2006.01) |
| B01D 71/06 | (2006.01) |
| B82Y 5/00 | (2011.01) |
| G01N 33/543 | (2006.01) |
| B01L 3/00 | (2006.01) |

(52) U.S. Cl.
CPC ......... *G01N 33/54373* (2013.01); *B01L 3/5027* (2013.01); *B01L 3/502753* (2013.01); *Y10S 977/904* (2013.01); *Y10S 977/92* (2013.01); *Y10S 977/958* (2013.01)
USPC .............. 435/287.1; 210/500.21; 210/500.26; 210/500.35; 977/904; 977/920; 977/958

(58) Field of Classification Search
USPC ........ 435/287.1; 210/500.21, 500.26, 500.35; 977/904, 920, 958
See application file for complete search history.

(56) References Cited

U.S. PATENT DOCUMENTS

| | | | |
|---|---|---|---|
| 2002/0117659 | A1 | 8/2002 | Lieber et al. |
| 2003/0183576 | A1 | 10/2003 | Ohara et al. |
| 2004/0029258 | A1 | 2/2004 | Heaney et al. |
| 2005/0145570 | A1 | 7/2005 | Pipes |
| 2005/0178720 | A1 | 8/2005 | Pluester et al. |
| 2006/0118491 | A1 | 6/2006 | Gjerde et al. |
| 2006/0269927 | A1 | 11/2006 | Lieber et al. |
| 2006/0278580 | A1* | 12/2006 | Striemer et al. .............. 210/650 |

OTHER PUBLICATIONS

S. D. Noblitt et al., Integrated Membrane Filters for Minimizing Hydrodynamic Flow and Filtering in Microfluidic Devices, 79 Anal. Chem. 6249-6254 (2007).*
PCT Search Report—Dec. 24, 2008.

* cited by examiner

*Primary Examiner* — Randy Boyer
(74) *Attorney, Agent, or Firm* — Seema S. Katragadda

(57) ABSTRACT

A composite detection device having in-line desalting is provided. The composite detection device comprises a membrane configured for desalting at least a portion of an analyte stream, and a nanostructure for detecting a bio-molecule or a bio-molecule interaction, wherein the nanostructure and the membrane are arranged such that an analyte stream desalted at least in part by the membrane is detected by the nanostructure. A bio-sending detection system having the composite detection device and method of fabrication of the composite detection device are also provided.

16 Claims, 6 Drawing Sheets

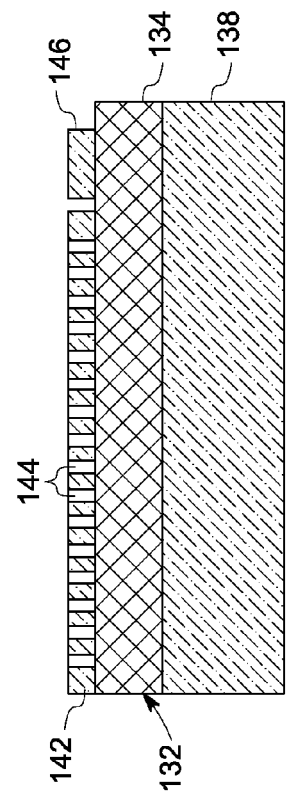
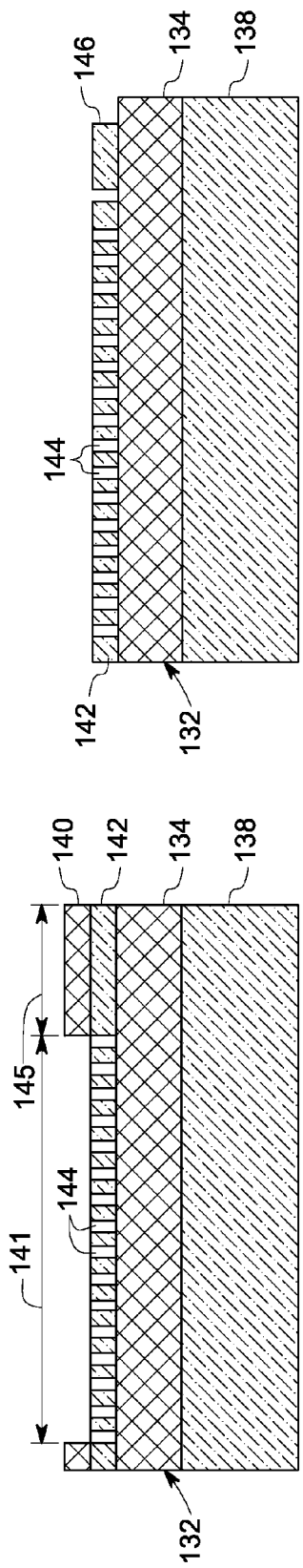
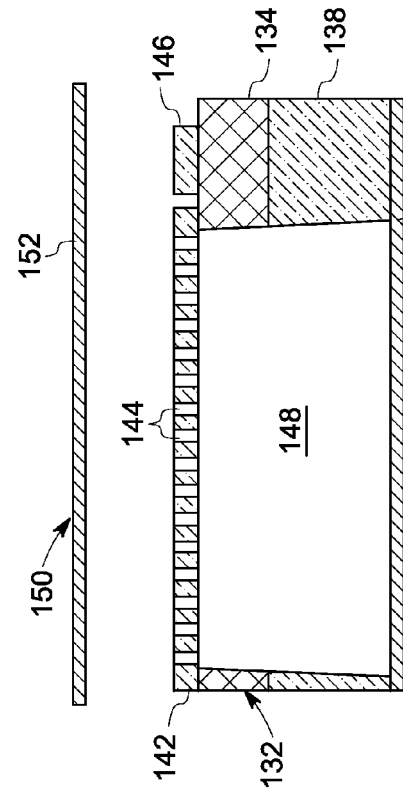

COMPOSITE DETECTION DEVICES HAVING IN-LINE DESALTING AND METHODS OF MAKING THE SAME

BACKGROUND

The invention relates to devices for detecting bio-molecules and/or bio-molecules interactions and methods of making the same, and more particularly to such detection devices having in-line desalting and methods of making the same.

Proteomics offers great potential for discovering biomarker patterns for earlier screening and detection of lethal and infectious diseases, systematic monitoring of physiological responses to drugs, and selecting the best treatment options for individual patients. For routine clinical use, an inexpensive, easy-to-use, multiplexed and high throughput protein analysis platform is needed, with high sensitivity and specificity for detection of low-abundance biomarkers in serum or other body fluids. There is also a need for high throughput and highly integrated sensor arrays for drug screening.

Nanostructured sensor arrays that use purely electrical detection, such as a field effect transistor (FET), fabricated with Si or other semiconductors, offer some of the desired characteristics. In such a device, a device channel of Si or other semiconductors is defined between two electrodes. The surface of the semiconductor channel or its oxide surface may be modified and covalently functionalized with antibodies or other receptor ligands for quantitative biorecognition. The binding of protein or other biomolecules induces net charge change, or change in dipole moment and binding-induced dipoles or modification of energy distribution and/or density of surface states. These binding events can change surface potential of the FET device and therefore modulate the conductance of the semiconductor channel. A small voltage or current, small enough not to disturb biomolecule interactions, is applied between two electrodes, and the change in conductance of the device channel is related and calibrated to the analyte concentration in a solution. When the device channel is reduced to nanoscale, the detection limit can be significantly reduced due to increased surface-to-volume ratio. Further, the response time can also be reduced due to favorable mass transport at low analyte concentrations due to small binding capacity of the small sensing surface. The ultra low detection limit of the nano-FET sensor at low ionic strength solutions has been recently demonstrated.

However, these devices may be rendered ineffective due to the screening effect in higher ionic strength solutions. The Debye screening length is defined as the distance from the sensing surface where potential change can be detected by the sensing device. In a high ionic strength solution, the screening length is reduced by ions and thus, binding events occurring beyond the screening length cannot be detected. It has been shown that it is required to desalt the sample to sensitively detect the antigen since the physiological salt concentration can overwhelm the change in local charge brought about by the binding of the antigen to the antibody. This arises because at physiological concentrations of salt (~200 mM), the debye shielding layer is reduced to ~1 nm. An antibody molecule is approximately 10 nm in size, therefore the binding event is outside the debye layer thickness.

Samples can be desalted offline by repeated concentration and dilution on an ultrafiltration membrane in a centrifuge tube designed for this purpose. Alternatively, dialysis can be used, however, the process is slow. Samples can also be desalted in gel filtration columns but low molecular weight species can be lost with the salts and the process dilutes the sample, which is undesirable for high sensitivity analysis.

It would be desirable to provide a method and a device that would enable in-line/on-chip desalting for nano-FET biosensor while avoiding the need to desalt the sample offline since this step complicates the implementation of such a detector in a variety of applications (e.g. point-of-care).

BRIEF DESCRIPTION

In one embodiment, a composite detection device having in-line desalting is provided. The composite detection device comprises a membrane configured for desalting at least a portion of an analyte stream, and a nanostructure for detecting a bio-molecule or a bio-molecule interaction, wherein the nanostructure and the membrane are arranged such that an analyte stream desalted at least in part by the membrane is detected by the nanostructure.

In another embodiment, a bio-sensing detection device is provided. The bio-sensing detection device comprises a porous silicon membrane capable of at least partially desalting a stream having an analyte, and a silicon nanosensor for detecting the analyte disposed adjacent to the porous silicon membrane.

In yet another embodiment, a bio-sensing detection system having in-line desalting is provided. The bio-sensing detection system comprises a detection device having a porous membrane configured to desalt an analyte solution by diffusion, and a nanosensor disposed adjacent to the porous membrane, wherein a change in electrical conductivity of the nanosensor indicates a detection of an analyte by the nanosensor. The system further includes a signal processing unit for detecting the change in electrical conductivity of the nanosensor upon detection of an analyte.

In another embodiment, a point of care diagnostic device having a composite detection device of the present technique is provided.

In another embodiment, a method of fabrication of a composite detection device is provided. The method includes providing a layered structure having a substrate layer, an insulator layer and a top semiconductor layer, forming nanopores in a first portion of the top semiconductor layer, patterning a second portion of the top semiconductor layer to form a nanosensor, and patterning the insulator layer and the substrate layer to form a fluidic channel below the first portion of the top semiconductor layer.

DRAWINGS

These and other features, aspects, and advantages of the present invention will become better understood when the following detailed description is read with reference to the accompanying drawings in which like characters represent like parts throughout the drawings, wherein:

FIGS. 5-12 are schematic views illustrating a method of fabrication of a composite detection device of the present technique.

DETAILED DESCRIPTION

Figure 1:
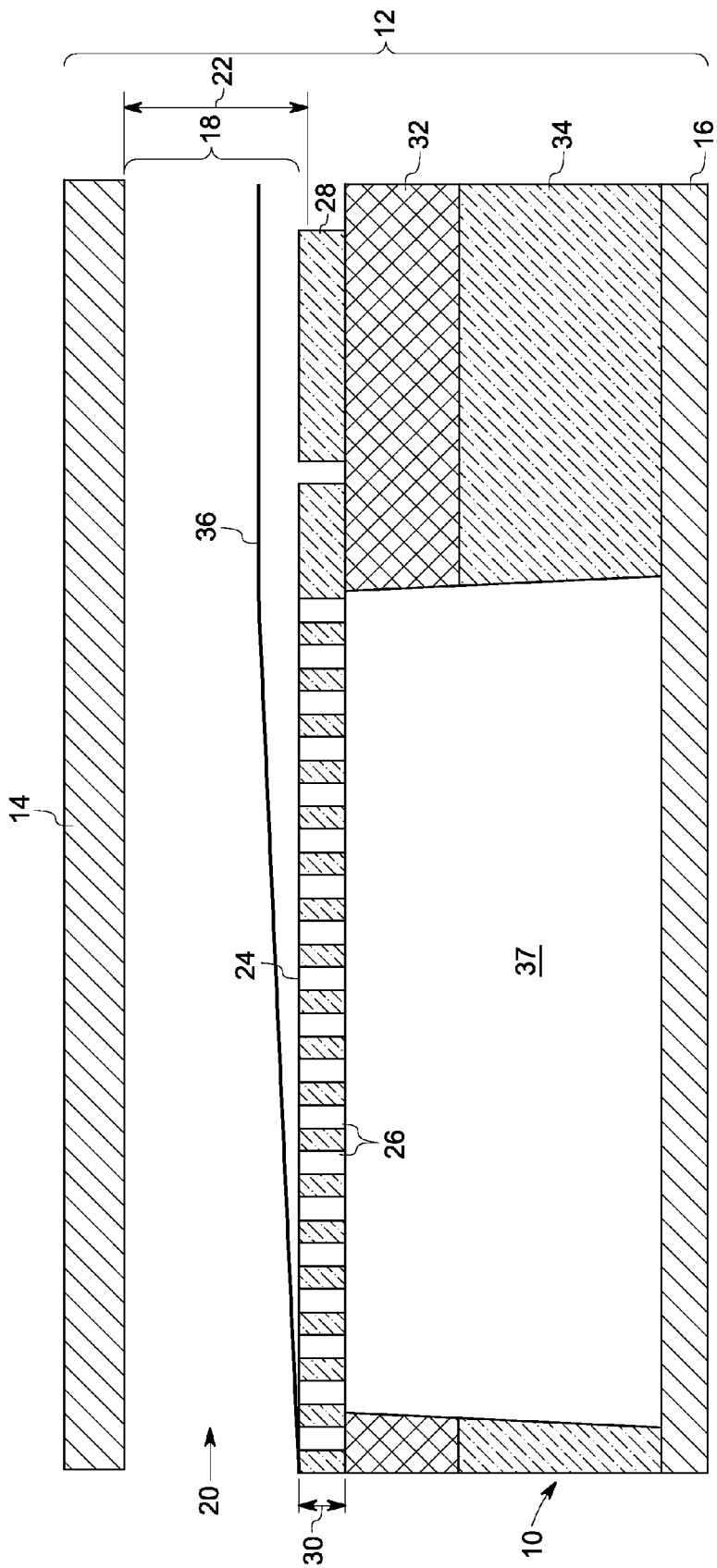
FIG. 1 is a cross-sectional side view of a localized desalting composite detection device disposed in a microfluidic device.

Embodiments of the present technique relate to in-line desalting and detection of an analyte solution to detect presence or absence of an analyte of interest. A composite detection device having provision for in-line desalting of an analyte solution comprises a membrane and a nanostructure. As used herein, the term "in-line desalting" refers to desalting of the solution/fluid in a continuous line along side a nanostructure for detecting an analyte. The term in-line desalting is not limited to desalting on-chip. The term nanostructure includes, but is not limited to, nanowire, nanowire channel, perforated semiconductor channel, nanopores, and structure comprising nanopores in the channel. The solution to be detected for the presence or absence of the analyte in the solution is first introduced to the membrane, which is configured for desalting at least a portion of the analyte stream. Subsequently, the analyte stream desalted at least in part by the membrane is detected by the nanostructure. As used herein, the term "detect" refers to determining the physical presence of the analyte in the solution and/or quantitative detection of the analyte in the solution.

The solution may include a biological or a non-biological sample. For this application, the composite detection device when used for biological purpose may be referred to as a bio-sensing detection device. The solution may include cells, tissue, biopsies, urine, ocular fluid, cerebro-spinal fluid, saliva, serum, blood, organ donation sample, material meant for human/livestock consumption, such as water, food, milk. The bio-sensing detection device may detect proteins, antibodies, peptides, viruses, nucleic acids (e.g., DNA, RNA), etc.

In one embodiment, the detection device includes a nanosensor with at least one semiconductor nanowire channel. The terms "nanostructure" and "nanosensor" may be used interchangeably throughout the application, and may include a nanowire channel or a perforated semiconductor channel. As used herein, the term "nanowire" refers to any elongated semiconductive structure that includes one or more cross sectional dimension that is less than 1000 nanometers, or preferably 100 nanometers. In some embodiments, the nanowire may be a single crystal nanowire. As used herein, the term "nanowire" may also refer to other elongated nanostructures, such as nanorods, nanotubes, nanoribbons, and the like. As used herein, the term "nanorod" refers to an elongated semiconductive structure similar to a nanowire but having an aspect ratio (length:width) less than that of a nanowire. Further, the nanowire may have any geometrical shape as the cross-section. Further, the cross-section of the nanowire may be uniform or non-uniform throughout the entire length of the nanowire. In another embodiment, the detection device includes a nanosensor with nanopores in its semiconductor channel.

In some embodiments, the nanosensor may be made of silicon. The selection of a material of the nanosensor may depend upon the ease of fabrication of the composite detection device. Alternatively, the material of the nanosensor may be selected depending upon the ease of functionalizing the surface of the nanosensor for the analyte of interest.

The nanosensor may include one or more nanowires arranged in a determined fashion. In some embodiments, the nanowires may be doped. For example, if a nanowire is made of a semiconductor material having low electrical conductivity, the nanowire may be doped to enhance the electrical conductivity of the nanowire. Non-limiting examples of dopants for nanowires may include phosphorous, boron, aluminum, arsenic, antimony, or combinations thereof. The nanowires may be doped either n-type or p-type.

The presence of an analyte in an analyte stream may be detected by determining a change in an electrical characteristic of the nanowire. As will be appreciated, the conductance of the nanowire is perturbed by the local charge in the near vicinity of the nanowire. For example, if a molecule such as an antibody is immobilized on the nanowire and an antigen with affinity to this antibody is present in the stream, the incoming antigen can specifically bind to the antibody that changes the surface potential of the nanowire and thus be detected by a change in the conductance of the nanowire. The nanowire may be functionalized to facilitate binding of the analytes to the surface of the nanowire. During functionalization, the nanowire may be provided with surface functional moieties. Non-limiting examples of such groups may include proteins, antibodies, nanobodies, affibodies, aptamers, nucleic acids, enzymes, antigens, polymer chains, or combinations thereof. Binders may be attached to the surface of the nanosensor by functionalization by chemical groups, such as —COOR, —OH, —COSH, —CHO, —NH$_2$, —CHO, —CN, halide, or combinations thereof. The nanowire may be coated with a coating to functionalize the nanowire. The coatings may include, but are not limited to, a metal, a semiconductor, or an insulator.

The membranes used in the composite detection device may at least partially desalt the analyte solution by diffusion mechanism. The membrane may be made of inorganic materials such as semiconductors or insulators. The membrane may be made of a porous material. For example, the membrane may be made of porous silicon. In some embodiments, the membrane and the nanosensor may be made of the same material. For example, the membrane and the nanowire may be made of silicon. Using the same material for the membrane and the nanowire may ease the fabrication and enable simultaneous fabrication of both the components, namely the membrane and the nanosensor.

The composite detection device may be disposed in a microfluidic channel, which is a part of a detection system for analyzing a biological solution. In one embodiment, the composite detection device of the present technique may be employed in a point of care diagnostic device.

Other than the membrane and a nanosensor, the composite detection device also includes one or more salt sinks, wherein the salt sinks are at least partially disposed beneath the membrane. The salt sinks comprise the membrane on one side and a base layer on the opposite side. The base layer may be one of the walls of the microfluidic device used to seal the microfluidic channel. The base layer comprises semiconductors, polymers or insulators, such as silicon, poly di-methyl siloxane (PDMS) or glass. In one embodiment, the salt sink comprises water or a buffer solution having low ionic strength. In another embodiment, the salt sink is a fluidic channel comprising water or a buffer solution having low ionic strength.

As will be described in detail below with regard to FIGS. 1-3, the composite detection device may comprise a localized desalting, or a bulk desalting, or a combination of both. As used herein, the term "localized desalting" refers to desalting that occurs in a thin layer/portion of the solution that is proximate to the membrane and comes in contact with the detection device. As used herein, the term "bulk desalting" refers to desalting of the bulk solution and transporting ions through the membrane by concentration gradient or charge selectivity. Bulk desalting may employ on-chip desalting. When the membrane is thin (1 nm to 100 nm, preferably 10 nm to 30 nm), ions in the analyte solution can pass through the membrane with little resistance. Since the concentration gradient is greatest between two sides of the membrane and there is little mixing in the microfluidic channel due to laminar flow, a thin layer of the analyte with significantly less ions can form on the membrane. The thickness of this layer grows with time (as the analyte solution passes along the membrane). For bulk desalting, the top microfluidic channel is thinner (comparable to the thin layer formed in the localized desalting situation) and wider (to accommodate the analyte) so the bulk analyte is desalted. For bulk desalting, the mixing of the analyte could be enhanced by acoustic wave to diffuse more ions through the membrane. In one embodiment, the analyte solution comprises more than one analyte and is at least partially desalted by at least one porous membrane. More than one nanosensor may be disposed adjacent to the membrane for multiplexed detection.

FIG. 1 illustrates a composite detection device 10 configured for localized desalting of the analyte stream. In the illustrated embodiment, the device 10 is disposed in a microfluidic device 12 defined by walls 14 and 16. The upper and lower walls 14 and 16, respectively, of the microfluidic device 12 may be made of materials, such as, but not limited to silicon, poly di-methyl siloxane (PDMS), glass, poly(methyl methacrylate) (PMMA). The presence of the composite detection device 10 in the microfluidic device 12 provides for microfluidic channel 18 in which the analyte stream flows in the direction illustrated by the arrow represented by reference numeral 20. The microfluidic channel 18 has a height 22 in a range from about 10 microns to about 1000 microns, and preferably from about 50 microns to about 300 microns. The analyte stream is a laminar flow in the microfluidic channel 18.

As illustrated, the composite detection device 10 includes a porous membrane 24 having a plurality of pores 26. The size of the pores 26 may be in the nanoscale range. Further, the density of the pores 26 may be in a range from about $10^{10}$ cm$^{-2}$ to about $10^{12}$ cm$^{-2}$. The thickness 30 of the membrane 24 may be in a range from about 1 nm to about 1000 nm, and preferably from about 10 nm to about 100 nm. The average physical size/diameter of nanopores is controlled to less than 10 nm or preferably less than 7 nm for desalting. The composite detection device 10 further includes a nanosensor 28. Although not illustrated, the nanosensor 28 may include one or more nanowires. The nanowires may be configured to interact with the analyte of interest. The nanowires may bind the molecules of the analyte to the surface of the nanowire, which causes a change in electrical conductance of the nanowire, thereby indicating presence of the analyte in the solution and determining the concentration of the analyte. As mentioned above, the surface of the nanowires may be functionalized to interact with the analyte.

The membrane 24 and the nanosensor 28 of the composite detection device 10 are disposed on a patterned insulator layer 32. The patterned insulator layer 32 in turn is disposed on a patterned semiconductor substrate 34. In one embodiment, the membrane 24, the nanosensor 28, and the patterned semiconductor substrate 34 are made of same material, such as silicon. In this embodiment, the insulator layer 32 may be made of silicon dioxide.

A membrane (such as membrane 24) immediately prior to the nanosensor 28 on the same lower wall 16 of the microfluidic device 12 as the nanosensor 28 may desalt the fluid in that layer presented to the nanosensor 28. The flow in the microfluidic channel 18 is generally laminar flow. Laminar flow in the channel minimizes the mixing between layers and it is known that such layers can persist for some time under the right flow conditions. The layer closest to the surface of nanosensor 28 gets desalted (i.e., depleted of ions), the bold line 36 represents the increase in ion depletion as the analyte solution progresses from one end to the other end of the membrane 24. As illustrated, by the time a particular portion of the analyte solution reaches the nanosensor 28 after crossing the membrane 24, the ion concentration in that portion of the solution is at its lowest. Note that it is not necessary to totally desalt the layer since the Debye layer thickness increases as the salt concentration decreases.

The composite detection device 10 further includes a salt sink or a cross-flow channel 37, which is at least partially disposed beneath the membrane 24. The cross-flow channel 37 may be filled with either water or a low ionic strength buffer. The ions from the analyte solution are diffused into the water or the low ionic strength buffer of the cross-flow channel 37 through the membrane 24. Thus, the membrane 24 is kept free of the dissolved ions so that the membrane 24 is available for diffusion of more ions from the incoming solution.

Figure 2:
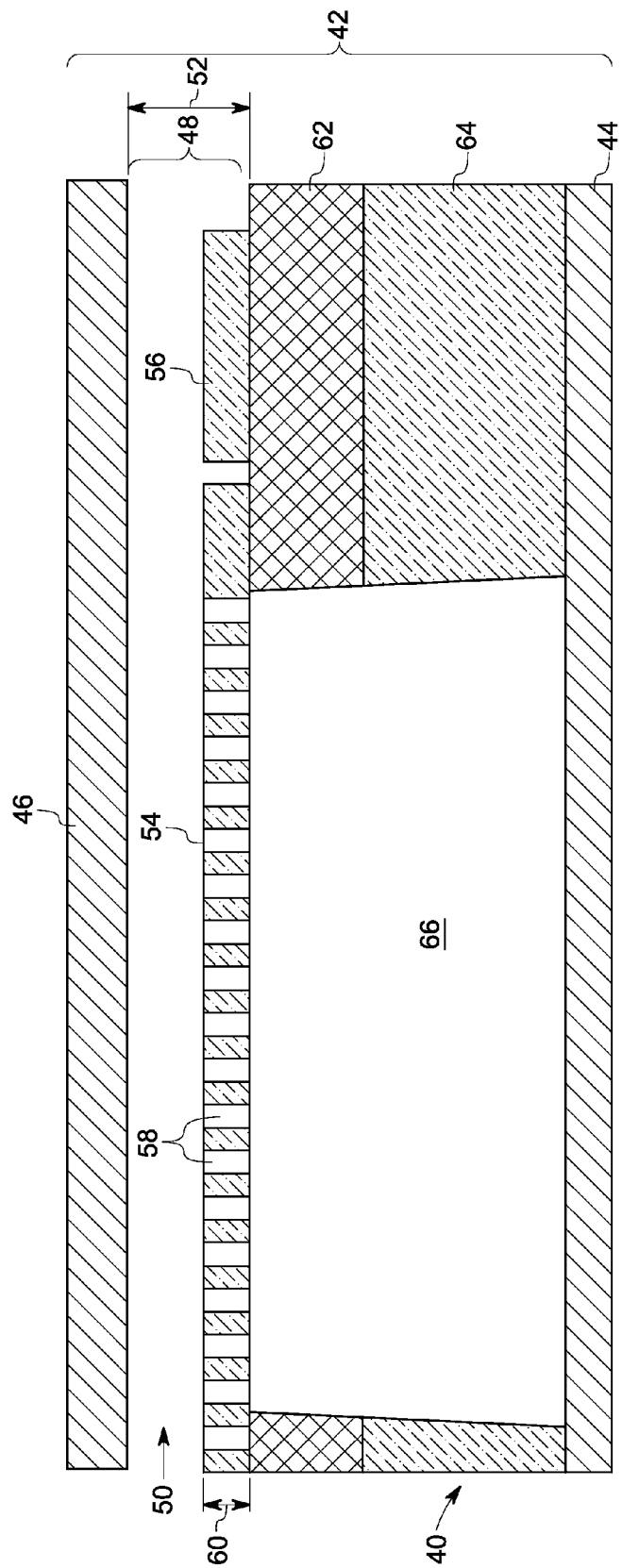
FIG. 2 is a cross-sectional side view of a bulk desalting composite detection device disposed in a microfluidic device.

FIG. 2 is a cross-sectional side view of a composite detection device 40, which is primarily used for bulk desalting. The composite detection device 40 is disposed in a microfluidic device 42 defined by walls 44 and 46. The presence of the composite detection device 40 in the microfluidic device 42 leaves a relatively thin microfluidic channel 48 for the analyte stream which flows in the microfluidic channel 48 in the direction represented by the arrow 50. The height 52 of the microfluidic channel 48 may be in a range of from about 50 nm to about 50 microns. The width of the microfluidic channel is kept sufficiently large so as to accommodate the sample volume. Acoustic waves may be used to enhance mixing for bulk desalting.

The composite detection device 40 includes a membrane 54 and a nanosensor 56. As with the membrane 24 of FIG. 1, the membrane 54 is a porous membrane having pores 58. The membrane 56 may have a thickness 60 in a range from about 1 nm to about 1000 nm, and preferably from about 10 nm to about 100 nm. As with the structure of FIG. 1, the composite detection device 40 includes a patterned insulator layer 62 and a patterned semiconductor layer 64 having a salt sink 66 disposed in between.

Figure 3:
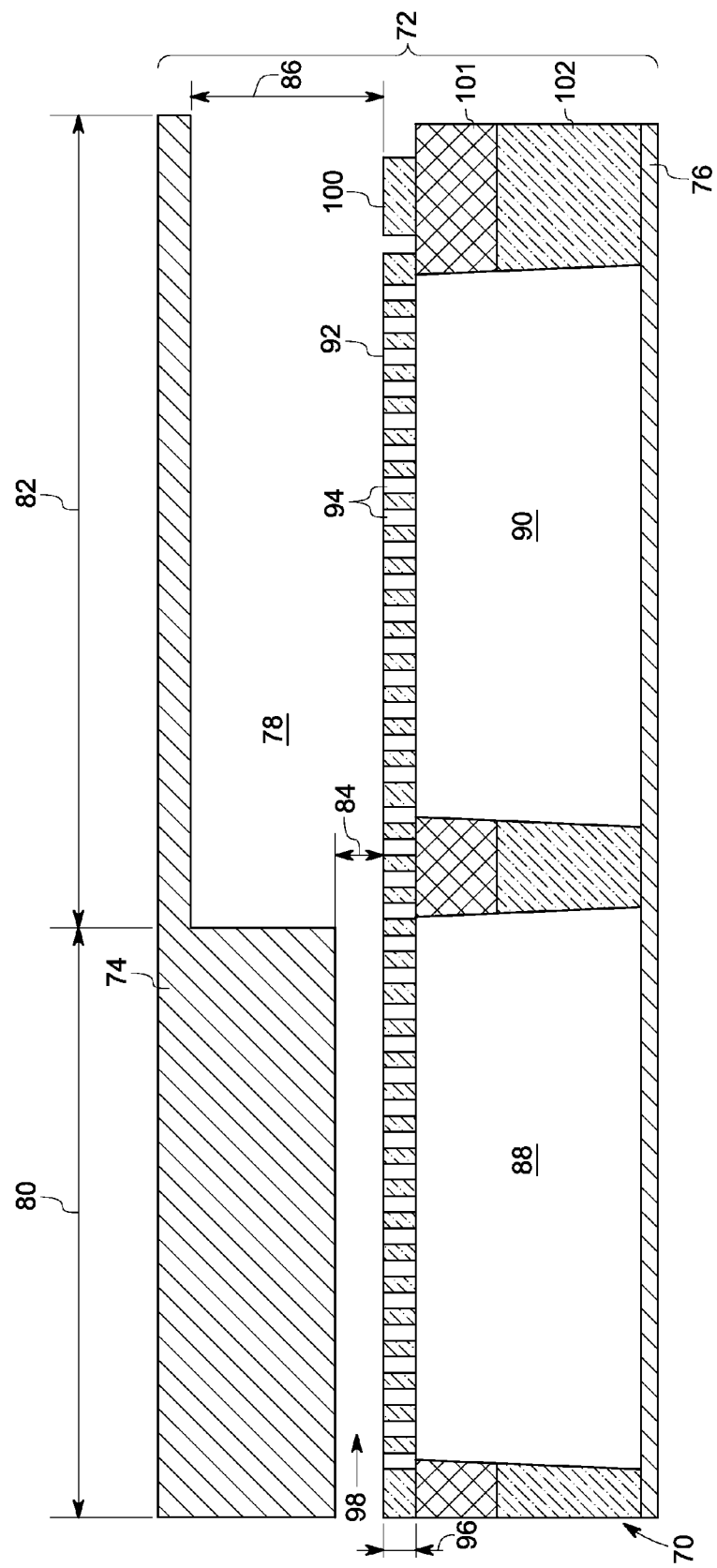
FIG. 3 is a cross-sectional side view of a composite detection device having provision for both localized and bulk desalting.

FIG. 3 illustrates a composite detection device 70 that is configured to perform both localized as well as bulk desalting for the analyte stream before the stream is detected for the presence or absence of an analyte of interest. The composite detection device 70 is disposed in a microfluidic device 72 defined by the walls 74 and 76. The microfluidic device 72 includes a microfluidic channel 78. The channel 78 has two different heights depending on the two different desalting regions 80 and 82. As illustrated, making the wall 74 with two different thicknesses provides the different heights of the microfluidic channel 78. The height of the microfluidic channel 78 depends upon the type of desalting area. For the bulk desalting region 80, the height 84 of the microfluidic channel 78 is less than that for the localized desalting region 82 (height 86). The bulk and localized regions 80 and 82 have individual salt sinks 88 and 90, respectively. In the illustrated embodiment, both the bulk and localized desalting regions 80 and 82 have a common membrane 92 extended over the two salt sinks 88 and 90. Although not illustrated, in one embodiment, the sinks 88 and 90 may also have separate membranes. Alternatively, the composite detection device 70 may have a common salt sink along with a common membrane for the localized and bulk desalting regions 80 and 82. Further, the membrane 92 contains a plurality of pores 94 and has a thickness 96. The direction of the flow of the analyte stream in the microfluidic channel 78 is represented by the arrow 98. The composite detection device 70 further includes a nanosensor 100. The membrane 92 and the nanosensor 100 are disposed on a patterned insulator layer 101 and a patterned semiconductor layer 102.

Figure 4:
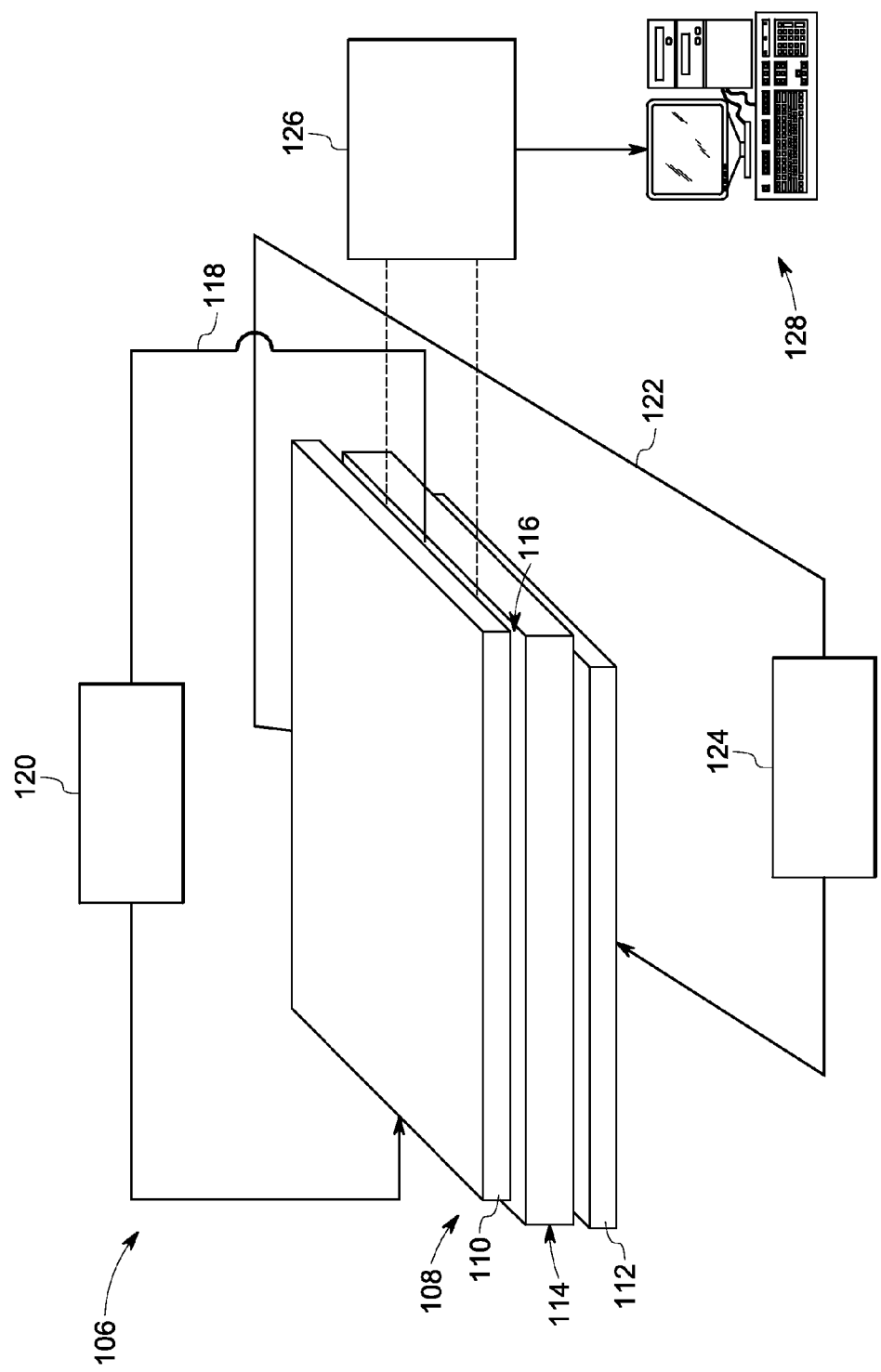
FIG. 4 is a schematic illustration of a sensing system having in-line desalting.

FIG. 4 is an example of a sensing system 106 having in-line desalting. The system 106 includes a microfluidic device 108 having an upper wall 110 and a lower wall 112. The layer 114 disposed in the microfluidic device 108 represents the composite detection device having a membrane and a nanosensor. Other components that may be used in the detection may include membranes to filter particulate matter, a buffer solution, and so on. In another aspect, the present disclosure provides a method for analyzing analytes in solution using the bio-sensing device described herein. The analyte stream is administered in the microfluidic channel 116 via the feed circuitry 118. The analyte stream may be driven in the microfluidic channel 116 by capillary force. Alternatively, a pumping device 120 may be employed to facilitate the analyte stream to drive in the microfluidic channel 116. Further, a second pumping device 124 is provided to remove ions that have diffused through the membrane via the circuitry 122. The system further includes a signal processing unit 126, which processes the signal received from the nanosensor when the nanosensor detects an analyte in the solution. As mentioned above, the detection device 114 measures the variation in electrical conductance due to the variation of the surface potential. In one embodiment, a reference device without antibody or other receptor molecules may be positioned close to the composite detection device. The response from the reference device may be subtracted from the response of the composite detection device to account for non-specific binding. The output signal of the processing unit 126 may then be seen on a display screen 128, such as a monitor. Alternatively, the output signal may be printed.

Figure 5:
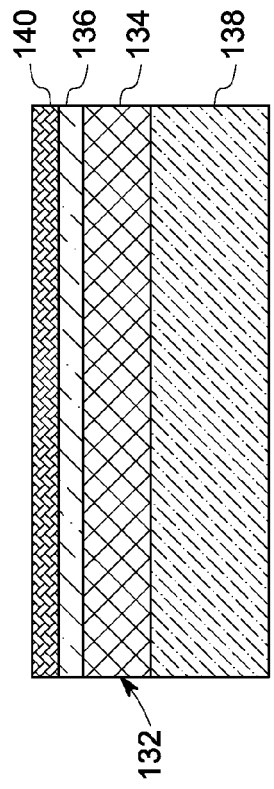
Figure 6:
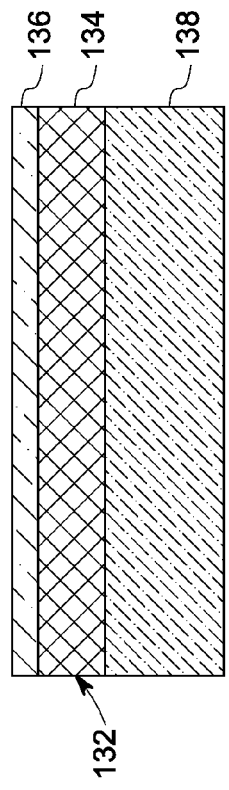
Figure 7:
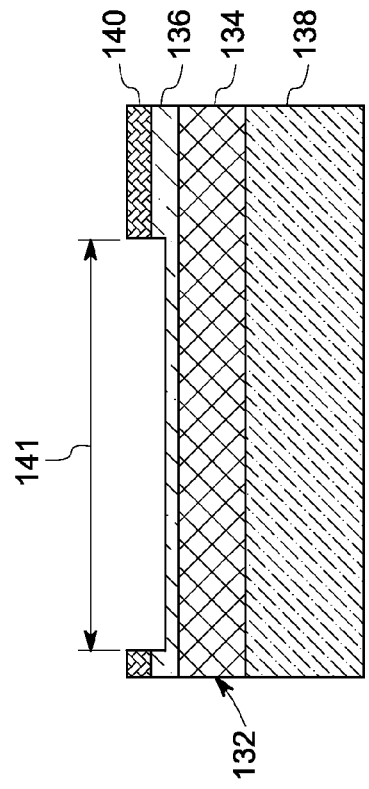
Figure 8:
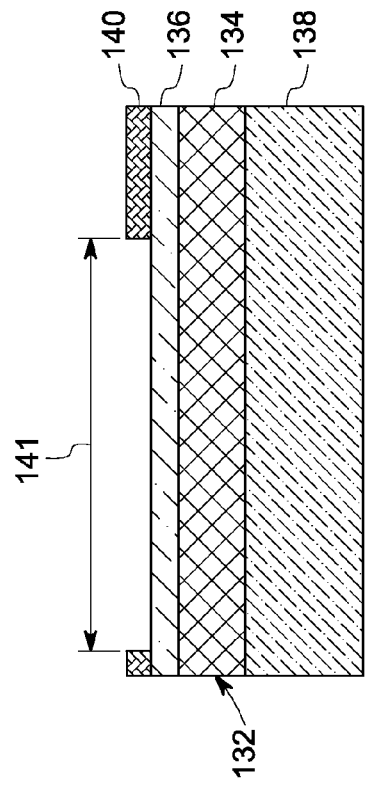

The devices discussed above with regard to FIGS. 1-4 may be fabricated using the fabrication method illustrated in FIGS. 5-12. As illustrated in FIG. 5, a layered structure having a substrate, an insulator layer and a top semiconductor layer is provided. For the purpose of this illustrated embodiment, the layered structure is a commercially available silicon-on-insulator (SOI) wafer 132. The wafer 132 has an insulator layer 134 disposed between a top silicon layer 136 and a silicon substrate 138. As illustrated in FIG. 6, a silica layer 140 may be disposed on the top silicon layer 136. The top silicon layer 136 may be thinned by thermal oxidation, for example. The resulted silica can be removed by a wet-etch process (buffered oxide etch, for example). Optionally, the silicon layer 136 for the silicon membrane may be further thinned to adjust the thickness of the membrane independent of the silicon thickness for the nanosensor. To perform this, a silica masking layer is formed by thermal oxidation of the silicon layer 136 or deposited by PECVD (plasma enhanced chemical vapor deposition) or LPCVD (low pressure chemical vapor deposition). Subsequently, as illustrated in FIG. 7, the silica layer 140 is patterned and the region 141 of the top silicon layer 136 is exposed. The exposed silicon may be thinned by wet etch. A combination of hydrofluoric acid, nitric acid and acetic acid may be employed for wet etch. Alternatively, one or more of KOH, EDP, TMAH may also be used for wet etch. The region 141 may also be thinned by employing plasma etch, reactive ion etch (RIE), ICP (inductively coupled plasma), ECR (electron cyclotron resonance), or CAIBE (chemically assisted ion beam etching)), or combinations thereof (FIG. 7). The exposed silicon may also be thermally oxidized and the resulted silica may be removed by wet etch of silica (buffer oxide etch for example) after stripping the photoresist (FIG. 8).

The next step is to form nanopores 144 in the region 141 while the silicon nanosensor region 145 is protected by the silica mask 140 (FIG. 9). The nanopores 144 may be formed by block copolymer nanolithography, or by other nanopatterning techniques (nanoimprint, soft lithography, block copolymer lithography, or e-beam lithography, etc.). Examples of suitable block copolymers include, but are not limited to, polystyrene-polybutadiene (PS-PB), postyrene-polyisoprene (PS-PB), polystyrene-b-poly(methyl methacrylate) (PS-b-PMMA), and the like. Block copolymers are composed of two different polymer chains covalently bonded together on one end. Polymers are usually immiscible with one another and phase-separate; in block copolymers, molecular connectivity forces phase separation to occur on molecular-length scales. As a result, periodically ordered nanometer-sized microdomains (such as cylinders or spheres) form, and their specific chemical, electrical, optical, or mechanical properties can be controlled by the choice of the constituent polymers. The sizes and periods of these microdomain structures are governed by the chain dimensions and are typically on the order of about 10 nm to about 30 nm. Structures smaller than 10 nm are also obtainable upon selection of appropriate blocks with a high Flory-Huggins interaction parameter and decreases the block lengths. For example, asymmetric polystyrene-polybutadiene (PS-PB) diblock copolymer in toluene solution can be spin-coated onto the SOI wafer and film thickness is controlled by varying spinning speed and polymer concentration. In bulk, the PS-PI separates into a spherical morphology and produces PI spheres) in PS matrix with body-centered-cubic order. The films are then annealed at 125° C., a temperature above their glass transition temperatures, for 24 hours in vacuum to obtain well-ordered morphologies. The micro-domain monolayer film is exposed to ozone to selectively degrade and remove the PB spherical domains before a $CF_4$ reactive ion etch (RIE) or $CF_4/O_2$ RIE. Ozone predominantly attacks the carbon-carbon double bonds in the PB backbone, cutting the bonds and producing PB fragments that can be dispersed in water. This results in regular spherical voids in the PS matrix and hence in a variation of the effective total thickness of the copolymer mask. The regions underneath the empty spheres are exposed to the RIE to produce holes in silicon, whereas the rest is still protected. Chlorine-based or fluorine-based reactive ion etching (RIE) is used to etch Si, with the copolymer film itself as the etching mask. Etching may be effected by several other techniques known in the art, such as electron cyclotron resonance (ECR) high density plasma etch or inductively coupled plasma (ICP) etch, chemically assisted ion beam etching (CAIBE), wet chemical etch, and the like. In certain embodiments, an inner diameter of the nanopores 144 may be modified by thermal oxidation. In some embodiments, the surface of the nanopores 144 may be functionalized. The effective pore size of the membrane is not only a function of the physical pore size but can be further modulated by surface charge in the pores. Surface charges can be modified by surface functionalization and is also a function of charge shielding and solution ionic strength. Functionalization of the nanopores 144 with large molecules can also reduce the effective pore size. Hydrophobic/hydrophilic functionalization of the surface of the pore may also affect porosity for various classes of molecules.

The silica protection layer 140 is completely or partially removed by wet etch (buffer oxide etch for example) after the nanopores are formed. The silicon nanowire channel 146 is then formed (FIG. 10). Photoresist is spun on the wafer and patterned. When the silica layer 140 is completely removed in the previous step, the exposed silicon layer is etched to underlying silica by a wet etch (HF+HNO₃+acetic acid, or KOH, or EDP, or TMAH) or plasma etch, RIE, ICP (inductively coupled plasma), ECR (electron cyclotron resonance), or CAIBE (chemically assisted ion beam etching)) or combination thereof. If the silica is partially removed, the silica can be used as etch mask with or without the photoresist in place.

Subsequently, the backside channel 148 is formed in the SOI wafer 132 (FIG. 11). Optional silica and SiNx can be formed on the backside as etch mask by thermal oxidation or PECVD or LPCVD. The backside of the channel 148 is patterned by conventional lithography. The exposed silicon can be etched by wet etch (11F+HNO₃+acetic acid, or KOH, or EDP, or TMAH) or plasma etch, RIE, ICP (inductively coupled plasma), ECR (electron cyclotron resonance), or CAIBE (chemically assisted ion beam etching)) or combinations thereof. The etch may be selectively stopped at the silica layer and the silica is then removed by a wet etch (buffered oxide etch for example). The microfluidic channel 150 having sides 152 and 154, made by PDMS polymer or glass or Si, can then be attached to the top surface and the backside (FIG. 12).

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A sensing system configured for in-line desalting of an analyte stream and sensing an analyte in the desalted analyte stream, comprising:
a microfluidic device comprising:
one or more microfluidic channels configured to define a flow direction of the analyte stream, wherein at least one microfluidic channel of the one or more microfluidic channels is configured for localized desaltin, bulk desaltin, or a combination thereof and wherein a height of a portion of the at least one microfluidic channel configured for the localized desalting is more than a height of a portion of the at least one microfluidic channel configured for the bulk desalting;
a microfluidic membrane having a surface that comprises a plurality of nanopores, wherein each of the plurality of nanopores comprises an upper opening into an interior portion of the at least one microfluidic channel, and wherein the microfluidic membrane is configured for desalting at least a portion of the analyte stream; and
a nanosensor having a surface that faces the interior portion of the at least one microfluidic channel, wherein the nanosensor is located downstream from the microfluidic membrane in the flow direction of the analyte stream, wherein the nanosensor is configured for sensing a bio-molecule or a bio-molecule interaction in the desalted analyte stream, and
wherein the nanosensor is in communication with a signal processing unit.

2. The sensing system of claim 1, wherein the microfluidic membrane and the nano sensor comprise silicon.

3. The sensing system of claim 1, further comprising one or more salt sinks, wherein the one or more salt sinks are at least partially disposed beneath the microfluidic membrane.

4. The sensing system of claim 3, wherein at least one of the one or more salt sinks comprises water or a buffer solution having low ionic strength.

5. The sensing system of claim 4, wherein at least one of the one or more salt sinks comprises the microfluidic membrane on one side and a base layer on an opposite side of the at least one of the one or more salt sinks.

6. The sensing system of claim 5, wherein the base layer comprises silicon, poly di-methyl siloxane (PDMS), glass, polymer or poly(methyl methacrylate) (PMMA).

7. The sensing system of claim 1, wherein respective portions of the at least one microfluidic channel corresponding to bulk desalting and the localized desalting are arranged such that the analyte stream is first desalted by the bulk desalting and then by the localized desalting before being detected by the nanosensor.

8. The sensing system of claim 1, wherein the nanosensor comprises a semiconductor channel.

9. The sensing system of claim 1, wherein the nanosensor comprises a perforated semiconductor channel.

10. The sensing system of claim 8, wherein a surface of the semiconductor channel is functionalized.

11. A sensing system configured for in-line desalting of an analyte stream and sensing an analyte in the desalted analyte stream, comprising:
a microfluidic device comprising;
one or more microfluidic channels configured to define a flow direction of the analyte stream, wherein at least one microfluidic channel of the one or more microfluidic channels is configured for localized desalting, bulk desalting, or a combination thereof, and wherein a height of a portion of the at least one microfluidic channel of the one or more microfluidic channels configured for the localized desalting is more than a height of a portion of the at least one microfluidic channel configured for the bulk desalting;
a porous silicon microfluidic membrane having a surface that comprises a plurality of nanopores, wherein each of the plurality of nanopores comprises an upper opening into an interior portion of the at least one microfluidic channel, and wherein the plurality of nanopores is configured for at least partially desalting the analyte stream; and
a silicon nano sensor having a surface that faces the interior portion of the at least one microfluidic channel, wherein the silicon nanosensor is located downstream from the porous silicon microfluidic membrane in the flow direction of the analyte stream for sensing the analyte disposed adjacent to the porous silicon microfluidic membrane, and
wherein the nanosensor is in communication with a signal processing unit.

12. The sensing system of claim 11, wherein the surface of the silicon nanosensor is functionalized.

13. The sensing system of claim 11, wherein the analyte stream comprises a laminar flow.

14. A bio-sensing system configured for in-line desalting of an analyte stream and sensing an analyte in the desalted analyte stream, comprising:
a bio-sensing device comprising a microfluidic device, wherein the microfluidic device comprises:
at least one microfluidic channel that defines a flow direction of the analyte stream, wherein the at least one microfluidic channel is configured for localized desalting, bulk desalting, or a combination thereof, and wherein a height of a portion of the at least one microfluidic channel configured for the localized desalting is more than a height of a portion of the at least one microfluidic channel configured for the bulk desalting;
a porous microfluidic membrane having a surface that comprises a plurality of nanopores, wherein each of the plurality of nanopores comprises an upper opening into an interior portion of at least one of the at least one microfluidic channel, and wherein the plurality of nanopores is configured for at least partially desalting an analyte solution by diffusion;

a nano sensor having a surface that faces the interior portion of the at least one of the at least one microfluidic channel, wherein the nanosensor is located downstream from the porous microfluidic membrane in the flow direction of the analyte stream and wherein a change in electrical conductivity of the nanosensor indicates a detection of the desalted analyte solution by the nano sensor; and a signal processing unit in communication with the nanosensor for detecting the change in electrical conductivity of the nano sensor upon sensing the analyte.

15. The bio-sensing system of claim 14, further comprising a pumping device configured to drive the analyte solution in the at least one microfluidic channel.

16. A point of care diagnostic device comprising a sensing system for in-line desalting of an analyte stream and sensing an analyte in the desalted analyte stream, wherein the sensing system comprises:

a microfluidic device comprising:

at least one microfluidic channel configured to define a flow direction of the analyte stream, wherein the at least one microfluidic channel is configured for localized desalting, bulk desalting, or a combination thereof, and wherein a height of a portion of the at least one microfluidic channel configured for the localized desalting is more than a height of a portion of the at least one microfluidic channel configured for the bulk desalting;

a microfluidic membrane having a surface that comprises a plurality of nanopores, wherein each of the plurality of nanopores comprises an upper opening into an interior portion of the at least one microfluidic channel, and wherein the microfluidic membrane is configured for desalting at least a portion of the analyte stream; and a nanosensor having a surface that faces the interior portion of the at least one microfluidic channel, wherein the nanosensor is located downstream from the microfluidic membrane in the flow direction of the analyte stream, wherein the nanosensor is configured for sensing a bio-molecule or a bio-molecule interaction in the desalted analyte stream, and wherein the nanosensor is in communication with a signal processing unit.

* * * * *